United States Patent [19]

Rosen et al.

[11] 4,248,792
[45] Feb. 3, 1981

[54] PROCESS FOR THE INTERCONVERSION OF CRYSTALLINE FORMS OF ETHYLENE BIS-STEARAMIDE

[75] Inventors: Marvin Rosen, Williamsport; Lloyd C. Franklin, Montgomery, both of Pa.

[73] Assignee: Glyco Chemicals, Inc., Greenwich, Conn.

[21] Appl. No.: 51,203

[22] Filed: Jun. 22, 1979

[51] Int. Cl.$^3$ .......................... C09F 5/00; C11C 3/00
[52] U.S. Cl. .................................. 260/404.5; 260/428
[58] Field of Search ............... 260/404.5 R, 404.5 PA, 260/428

[56] References Cited

U.S. PATENT DOCUMENTS 3,677,963  7/1972  Lichtman ..................... 252/321 X

OTHER PUBLICATIONS

Sakwrai, T., Chem. Absts. vol. 50, No. 6125 (1956).
Kornev, K., et al., Chem. Absts. vol. 67, No. 9002 (1965).

Primary Examiner—John F. Niebling
Attorney, Agent, or Firm—Cushman, Darby & Cushman

[57] ABSTRACT

A process for preparing alpha and beta crystalline forms of N,N'-ethylene bis-stearamide (EBS). Heating of EBS at temperatures of 120°–160° C. to melt the EBS results in formation of 95+% alpha which when cooled to 40° C. or less remains in the alpha state, but upon reheating to about 80° C. results in 95+% conversion to the beta crystalline form. Heating of the alpha crystalline form at temperatures ranging from about 45°–90° C. for selected periods of time results in mixtures of alpha and beta.

27 Claims, 2 Drawing Figures

PROCESS FOR THE INTERCONVERSION OF CRYSTALLINE FORMS OF ETHYLENE BIS-STEARAMIDE

BACKGROUND OF THE INVENTION

The present invention relates to the interconversion of crystalline forms of N,N'-ethylene bis-stearamide (EBS).

The crystalline structure of fatty acids has been described by K. S. Markley, Fatty Acids—Their Chemistry, Properties, Production and Uses, Part 4, Chapter XXII, and Part 1, Chapter IV, Interscience Publishers, 1967. Associated thermal properties of fatty acids have been reported also by Markley.

The crystalline state of long chain acid amides and the changes which occur on heating have been studied to a limited degree by J. D. Turner, Univ. Microfilms, Publ. No. 7205, Ann Arbor, Mich., and J. D. Turner and E. C. Lingafelter, Acta. Cryst. 8 549–50 (1955); Chem. Abst. 49, 15352. Single-crystal x-ray studies of even carbon number fatty acid amides from $C_{10}$ to $C_{28}$ showed three phases, all stable at room temperature. Irreversible changes were reported by T. Sakurai, J. Phys. Soc. Japan 10, 1040–8 (1955); Chemical Abstracts 50, 6125. Comparison of iso acids, explanations for the physical configuration of the crystalline states and differences in the numbers of states have been investigated (See K. E. Arosenius, et al, Arkiv Kemi, Mineral Geol. 26A No. 19–20 (1048); Chem. Abst. 44, 3883, and S. Kurokawa, Bull. Chem. Soc. Japan 28, 660–4 (1955); Chem. Abst. 50, 6868) along with some correlative exploration of the infrared differences found for different molecular orientations (See P. A. Chollet, et al, Report 1975, CEA-N-1814. ERDA Energy Res. Abstr. 1976, 1(6); Chem. Abst. 86, 29112; and K. Machida, Spectrochim. Acta, Part A 1972, 28(2), 235–56; Chem. Abst. 70, 78705X). These sources, as cited in Chemical Abstracts do not describe studies of fatty acid long chain diamides in respect to crystalline structure and associated thermal or spectral relationships.

Bis-amides of fatty acids are known to be useful lubricants and in the production of polymeric materials such as polyvinyl chloride. These bis-amides are particularly useful in the preparation of defoamer compositions as described in U.S. Pat. Nos. 3,652,453; 3,673,105; 3,677,963; 3,935,121; 3,951,853; 3,990,905; 4,032,473; and 4,088,601. A preferred bis-amide for such applications is N,N'-ethylene bis-stearamide.

Unfortunately, the use of bis-amides as noted above has not been entirely trouble free. For example, one of the major concerns in the preparation and use of defoamer compositions is to provide an efficient defoamer which does not gel prior to use.

We have found that there is a need in paper defoamer use, some plastic applications and preparation of lubricants for essentially pure compositions of EBS and other bis-amides of a single discrete crystalline form or mixtures thereof. Prior to the present invention, the art has failed to provide a means for the preparation of crystalline forms of EBS in a controlled fashion suitable for large scale production.

Accordingly, it is the primary object of the present invention to provide a process for the production of N,N'-ethylene bis-stearamide in pure crystalline forms or mixtures thereof.

It is a further object of the present invention to provide a controlled means for large scale production of EBS in desired crystalline forms.

These and other objects of the invention will become more apparent from the discussion which follows.

SUMMARY OF THE INVENTION

The preparation of N,N'-ethylene bis-stearamide is well known and is generally carried out by the reaction of stoichiometric amounts of ethylene diamine and commercial stearic acid to form a molten product which is then solidified as described by the aforementioned U.S. Pat. No. 3,677,963, which is incorporated herein by reference. Commercial stearic acid will generally contain from about 45 to 95 percent by weight stearic acid, with the bulk of the balance being palmitic acid (i.e. from about 5 to 40 percent) and $C_{12}$–$C_{22}$ fatty acids. Thus, EBS as defined herein may be represented by the formula:

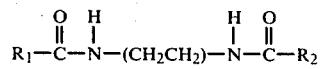

where $R_1$ and $R_2$, which may be the same or different, are saturated or unsaturated aliphatic groups having from 12 to 22 carbon atoms provided that at least about 45% of $R_1$ or $R_2$ are $C_{18}$. However, for the present process the content of the $C_{18}$ fraction does not appear to be critical.

While EBS has been found to have a number of crystalline forms, two are distinct and predominant crystalline forms, and are referred to herein as alpha ($\alpha$) and beta ($\beta$), each of which is characterized by a distinctive infrared spectrum as set forth in the following tables:

TABLE I

Infrared Characteristics of Crystalline EBS

| Wavelength, Microns | Wavenumber (CM$^{-1}$) | 100% $\alpha$EBS | 100% $\beta$EBS |
|---|---|---|---|
| 8 | 1250 | Absent | Sharp |
| 10–11 | 1000–909 | 10.4 | 10.55–10.6 |
| 13–15 | 769–666 | Absent | 13.4 |
|  |  | 13.75 | 13.75 |
|  |  | 14.7 | 14.2 |
| 16–17 | 625–588 | 17.0 | 16.0 |

TABLE II

EBS Composition Infrared Characteristics

| Frequency | | EBS Composition | | | | |
|---|---|---|---|---|---|---|
| Wave Length ($\mu$) | Wave Number (cm$^{-1}$) | 100%$\alpha$ | 75%$\alpha$ 25%$\beta$ | 50%$\alpha$ 50%$\beta$ | 25%$\alpha$ 75%$\beta$ | 100%$\beta$ |
| 8.0 | 1250 | A | MW | M(S) | M(S) | MS(S) |
| 10.4 | 960 | M | MW | MW | W | A |
| 10.55 | 945 | A | W | MW | MW | M |
| 13.4 | 745 | A | A | VW | W | W |
| 13.75 | 728 | MS | MS | MS | MS | MS |
| 14.2 | 705 | A | A | W | MW | M |
| 14.7 | 675 | MS | M | W | A | A |
| 16.0 | 635 | A | W | W | MW | MW |

TABLE II-continued

EBS Composition
Infrared Characteristics

| Frequency | | EBS Composition | | | | |
|---|---|---|---|---|---|---|
| Wave Length (μ) | Wave Number (cm$^{-1}$) | 100%α | 75%α 25%β | 50%α 50%β | 25%α 75%β | 100%β |
| 17.0 | 588 | M | MW | W | VW | A |

Relative Strength of Absorption
VW - Very weak
W - Weak
MW - Medium Weak
M - Medium
MS - Medium Strong
A - Absent
(S) - Sharp From the foregoing, it is noted that a distinguishing characteristic between the α and β forms in the infrared absorption at 1248 cm$^{-1}$, 955 cm$^{-1}$ and 940 cm$^{-1}$ which reveals the distinguishing characteristics noted in Table III below.

TABLE III

| | IR Wavenumber | | |
|---|---|---|---|
| | 1248 cm$^{-1}$ | 955 cm$^{-1}$ | 940 cm$^{-1}$ |
| α | Absent | Present | Absent |
| β | Present | Absent | Present |

FIGS. 1 and 2 represent infrared spectra of pure EBS α and EBS β forms respectively. The EBS sample was run on a Perkin Elmer 281 in KBr.

There are also other methods by which the alpha and beta forms can be distinguished including, but not limited to, X ray diffraction and differential scanning calorimetry (DSC). Thus, the DSC of the alpha form reveals transition peaks at 68° C. and 103° C. while the beta shows a transition at 109° C.

N,N'-ethylene bis-stearamide can be prepared in essentially pure α form by (a) heating N,N'-ethylene bis-stearamide to a temperature between about 140° and 160° C. for a period of time sufficient to convert the N,N'-ethylene bis-stearamide to the alpha crystalline form; and (b) cooling the heated product of step (a) to a temperature of 40° C. or less whereby at least 95% of the N,N'-ethylene bis-stearamide is recovered in the alpha crystalline form.

In accordance with the present invention, N,N'-ethylene bis-stearamide in the beta form may be prepared by:

(a) heating N,N'-ethylene bis-stearamide to a temperature of at least 120° C. for a period of time sufficient to convert all the N,N'-ethylene bis-stearamide to the alpha form;

(b) cooling the product of step (a) to a temperature of about 40° C. or less, whereby at least 95% of the cooled product is in the alpha form;

(c) heating the product obtained in step (b) to a temperature of from about 70° to 90° C. for a period of time whereby at least 95% of the product is converted to and recovered in the beta form.

The invention further provides for the preparation of N,N'-ethylene bis-stearamide in both alpha and beta form by heating N,N'-ethylene bis-stearamide in the alpha crystalline form to a temperature between about 45° and 90° C. for a period of time sufficient to convert at least a portion (e.g. 10%) of the N,N'-ethylene bis-stearamide to the beta crystalline form.

The invention also provides for a process for the production of N,N'-ethylene bis-stearamide in the alpha form comprising the steps of:

(a) heating N,N'-ethylene bis-stearamide in the beta form to a temperature of at least 120° C. for a period of time sufficient to convert the N,N'-ethylene bis-stearamide to the alpha crystalline form; and (b) cooling the heated product of step (a) to a temperature of 40° C. or less whereby at least 95% of the N,N'-ethylene bis-stearamide is recovered in the alpha crystalline form.

In addition one may prepare mixtures of alpha and beta forms of N,N'-ethylene bis-stearamide which comprises the steps of:

(a) heating N,N'-ethylene bis-stearamide to a temperature of at least 120° C. for a period of time sufficient to convert all the N,N'-ethylene bis-stearamide to the alpha form;

(b) cooling the product of step (a) to a temperature of about 40° C. or less, whereby at least 95% of the cooled product is in the alpha form;

(c) heating the product obtained in step (b) to a temperature of from about 45° to 90° C.;

(d) monitoring the conversion of the product; and (e) rapidly cooling the product of step (c) when the desired amount of beta form is produced whereby a product containing both alpha and beta forms is recovered.

DETAILED DESCRIPTION OF THE INVENTION

Figure 1:
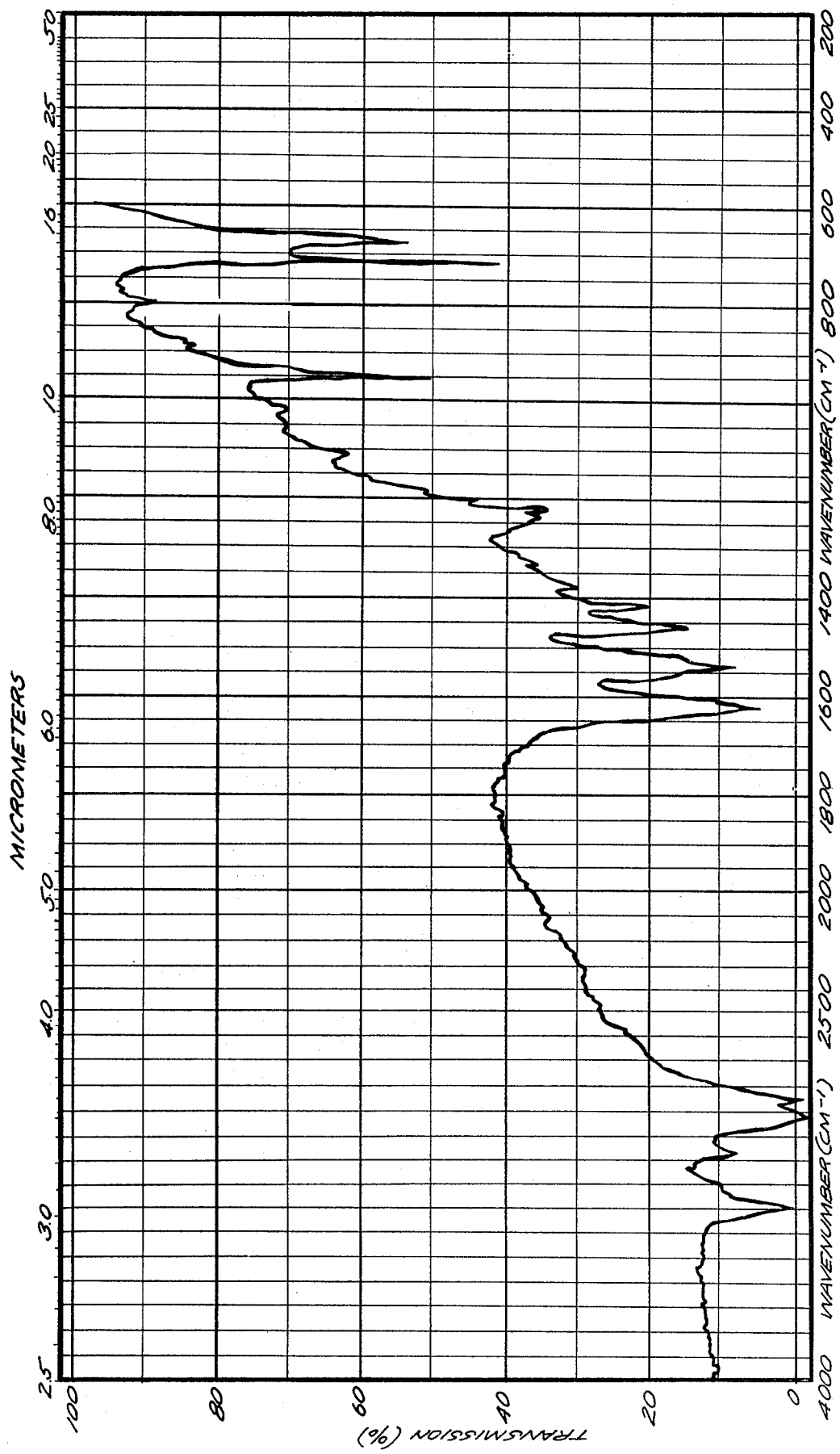
Figure 2:
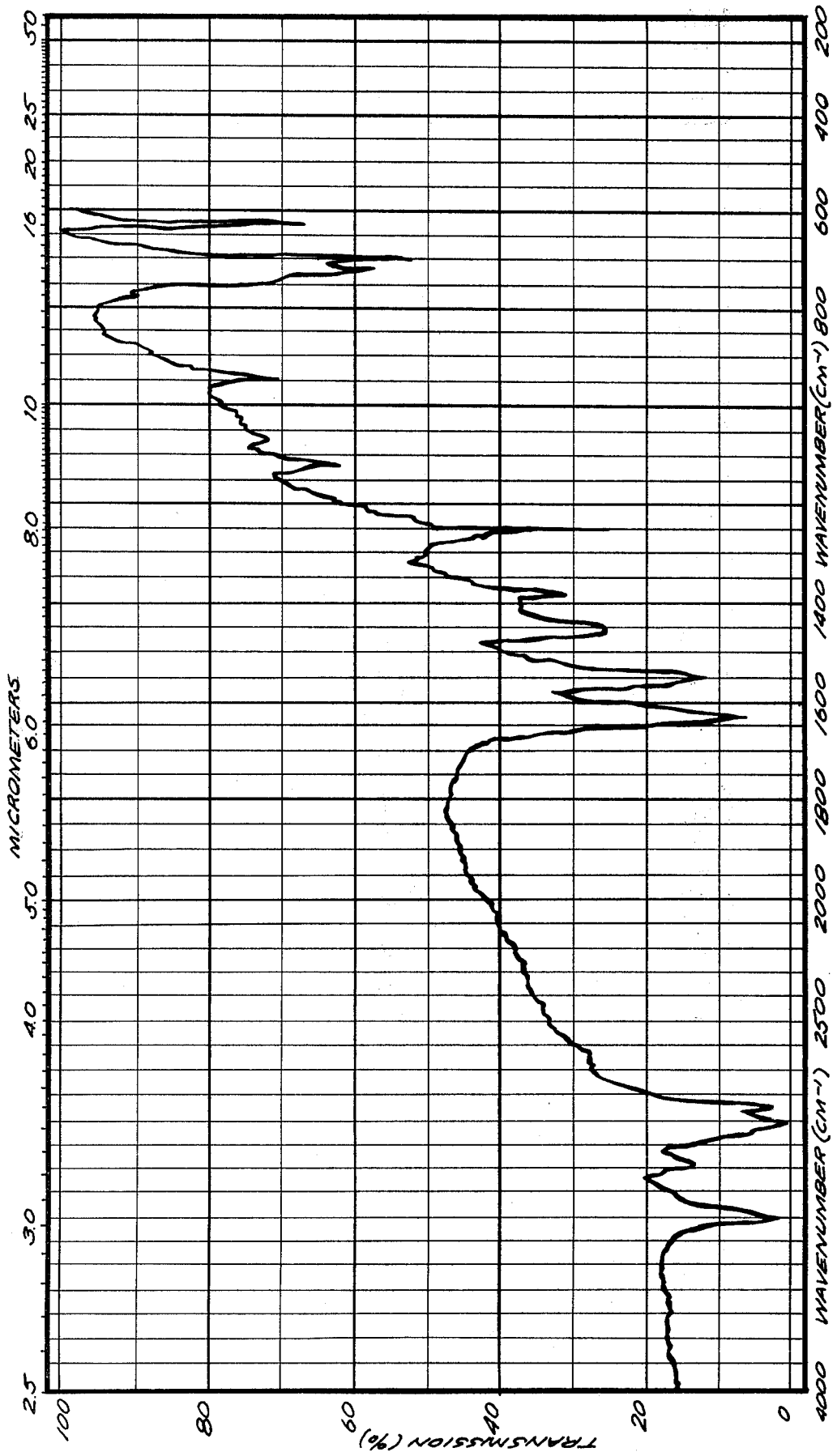

EBS, in the crystalline state whether in alpha, beta, or mixed form when heated to a temperature of at least 120° C., and preferably above the melting point of EBS (i.e. from about 140° to 160° C., and preferably about 150° to 155° C.) for a sufficient period of time (e.g., 5 minutes to 1 hour) undergoes a conversion whereby at least 95% of the EBS is in the alpha form. This form is stable at these temperatures and remains stable upon cooling to temperatures of 40° C. or less. Preferably, the heated EBS is rapidly cooled (i.e. less than 1 hour and most suitably less than 5 minutes).

Upon heating solid α EBS, starting at a temperature of 40° C. or less, to a temperature of from about 45° to 90° C. (preferably about 70° to 90° C. and most suitably 80° C.) for a sufficient period of time (e.g. about 1 to 72 hours) the EBS undergoes conversion to the beta crystalline form. Conversions of 95+% to the beta form occur readily at temperatures of about 70° to 90° C., preferably 80° C. By properly monitoring the conversion process, through such means as for example IR and DSC, one can easily obtain desired ratio mixtures of the alpha and beta form by merely halting the conversion through rapid cooling to less than 40° C., so as to remove residual heat therefrom which precludes any further transformations.

Heating the beta form to temperatures of at least 120° C., and suitably 140°-160° C. (e.g. 150°-155° C.) results in conversion to the alpha form. Upon cooling to 40° C. or less, the material remains in the α form.

Conversion of EBS from the alpha to the beta form occurs best when heated to about 80° C., with over 95% transformation. The time may vary for the conversion but generally will take from 1 to 72 hours depending on the physical state, i.e. size, configuration and shape, of the EBS material. Conversion takes place more rapidly the smaller the size of the EBS material which may for example be in the atomized, powder, bead, prill, flake or even block form.

For even more rapid conversion of alpha to beta, one may employ an inert solvent in the conversion process, such as isopropanol. In such instances the solid EBS alpha form is mixed with the inert solvent at a suitable concentration (e.g. about 5 to 10%) and brought to the boil (about 80°-85° C.) so as to completely dissolve the EBS. Thereafter, the solution is cooled to room temperature so as to allow the material to precipitate. The product is isolated in the beta form (95+%) by filtration and drying at ambient temperatures at a reduced pressure.

The following examples are offered to more fully illustrate the invention, but are not to be construed as limiting the scope thereof.

EXAMPLE 1

Ten grams of EBS (75% alpha—25% beta) when heated to 150° C. for 30 minutes is converted (95+%) to the alpha form as indicated by an infrared spectrum as set forth in Tables 1 and 2.

EXAMPLE 2

One gram samples of EBS, 95+% alpha form, were placed in an oven at 80° C. A sample was removed every half hour over a five hour period and an IR spectra was taken on selected samples with the following results:

| Time | EBS Crystalline Form |
|---|---|
| 2½ hours | 70% beta, 30% alpha |
| 4 hours | 75% beta, 25% alpha |
| 5 hours | >95% beta |

EXAMPLE 3

Ten grams of EBS 95+% beta were heated in an oven to a temperature of 155° C. until all the wax had melted. The material was then cooled to 40° C. and held at that temperature for a period of 3 hours. A sample was taken of the melt and found to be 95+% alpha. It was then heated to 80° C. for a period of two hours and an infrared spectra was taken. It was found that the material contained 95% beta form.

EXAMPLE 4

EBS, 95+% alpha, was placed in a circulating air oven at 155° C. for ½ hour. A small quantity of the melt was quickly cooled on aluminum foil and an IR spectra taken. The oven was then cooled to 80° C. and a sample removed from the oven every half hour for a period of 4 hours during which the temperature of 80° C. was maintained. The remainder of the EBS was left in the oven over a period of several days and removed after 78 hours. An IR was taken on selected samples and the results were as follows:

| Time | EBS Crystalline Form |
|---|---|
| Melt (Quick Cooled) | 95+% alpha |
| 4 hours | 95+% alpha |
| 78 hours | 95+% alpha |

EXAMPLE 5

The EBS material of Example 4 which had been heated for a period of 78 hours was cooled to room temperature and divided into two portions. One portion was ground in a mortar and pestle to a fine powder and the other was chopped into large pieces. Both portions were then placed in a heat circulating oven at 80° C. and sampled after four hours. The IR analysis revealed that for both portions there was a 40% alpha, 60% beta distribution.

EXAMPLE 6

1125 pounds of EBS (75% alpha, 25% beta) was heated in a rotary mixer at 45°-55° C. over a period of 3 to 4 hours, yielding an EBS product containing 57% alpha and 43% beta.

The interconversion of crystalline forms of EBS may be summarized according to the following schemes:

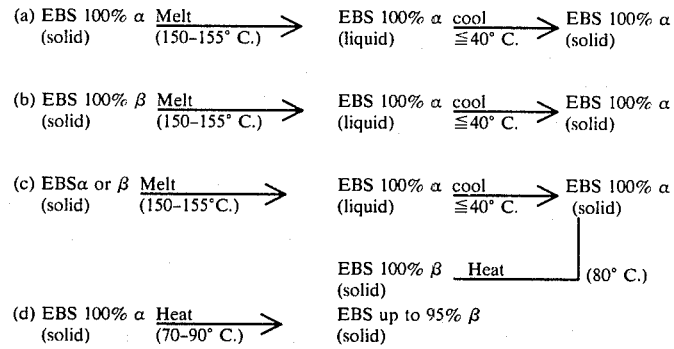

While the invention as described and claimed herein has been particularly directed to EBS, it is envisaged that the inter-conversion process would be applicable to other bisamides of the structure:

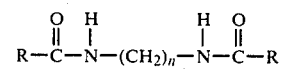

where:
n is an integer from 1–6; and
R is a saturated or unsaturated, straight or branched chain aliphatic group having from 5–22 carbon atoms.

The invention having been thus described, it is understood that departures can be made therefrom without affecting the basic process. It is understood that the present invention may comprise, consist, or consist essentially of the hereinabove recited steps and materials.

What we claim is:

1. A process for the preparation of alpha and beta forms of N,N'-ethylene bis-stearamide which comprises the steps of:
   (a) heating N,N'-ethylene bis-stearamide to a temperature of at least 120° C. for a period of time sufficient to convert all the N,N'-ethylene bis-stearamide to the alpha form;
   (b) cooling the product of step (a) to a temperature of about 40° C. or less, whereby at least 95% of the cooled product is in the alpha form; and
   (c) heating the product obtained in step (b) to a temperature of from about 70° to 90° C. for a period of time whereby at least 95% of the product is converted to and recovered in the beta form.

2. A process according to claim 1 wherein said heating in step (a) takes place at a temperature from about 150° to 155° C.

3. A process according to claims 1 or 2 wherein the cooling in step (b) is carried out in less than one hour.

4. A process according to claim 3 wherein the cooling is carried out in less than five minutes.

5. A process according to claims 1 or 2 wherein the said heating in step (a) is carried out for a period of from about 5 minutes to about one hour.

6. A process according to claims 1 or 2 wherein the heating in step (c) is carried out at a temperature of about 80° C.

7. A process according to claim 6 wherein the heating in step (c) is carried out for a period of from one to 72 hours.

8. A process according to claim 3 wherein the heating in step (c) is carried out for at least four hours.

9. A process for the production of N,N'-ethylene bis-stearamide in the beta crystalline form which comprises heating N,N'-ethylene bis-stearamide in the alpha crystalline form to a temperature between about 45° and 90° C. for a period of time sufficient to convert the N,N'-ethylene bis-stearamide to the beta crystalline form.

10. A process according to claim 9 wherein said heating is carried out at a temperature of about 80° C. for a period of time sufficient to achieve 95% conversion to the beta form.

11. A process according to claims 9 or 10 wherein heating is carried out for a period of from 1 to 72 hours.

12. A process according to claim 9 wherein upon conversion of between about 10 and 90% to the beta form, the bis-stearamide is rapidly cooled to a temperature of 40° C. or less to obtain a mixture of alpha and beta forms, the beta form being present in the range of 10 to 90% of the total product.

13. A process for the production of N,N'-ethylene bis-stearamide in the alpha form comprising the steps of:
   (a) heating N,N'-ethylene bis-stearamide in the beta form to a temperature of at least 120° C. for a period of time sufficient to convert the N,N'-ethylene bis-stearamide to the alpha crystalline form; and
   (b) cooling the heated product of step (a) to a temperature of 40° C. or less whereby at least 95% of the N,N'-ethylene bis-stearamide is recovered in the alpha crystalline form.

14. A process according to claim 13 wherein said heating takes place at a temperature from about 150° to 155° C.

15. A process according to claims 13 or 14 wherein cooling is carried out in less than one hour.

16. A process according to claim 15 wherein cooling is carried out in less than five minutes.

17. A process according to claims 13 or 14 wherein said heating is carried out for a period of from about 5 minutes to about one hour.

18. A process for the preparation of mixtures of alpha and beta forms of N,N'-ethylene bis-stearamide which comprises the steps of:
   (a) heating N,N'-ethylene bis-stearamide to a temperature of at least 120° C. for a period of time sufficient to convert all the N,N'-ethylene bis-stearamide to the alpha form;
   (b) cooling the product of step (a) to a temperature of about 40° C. or less, whereby at least 95% of the cooled product is in the alpha form;
   (c) heating the product obtained in step (b) to a temperature of from about 45° to 90° C.;
   (d) monitoring the conversion of the product; and
   (e) rapidly cooling the product of step (c) when the desired amount of beta form is produced whereby a product containing both alpha and beta forms is recovered.

19. A process according to claim 18 wherein said heating in step (a) takes place at a temperature from about 150° to 155° C.

20. A process according to claims 18 or 19 wherein the cooling in step (b) is carried out in less than one hour.

21. A process according to claim 20 wherein the cooling is carried out in less than five minutes.

22. A process according to claims 18 or 19 wherein the said heating in step (a) is carried out for a period of from about 5 minutes to about one hour.

23. A process according to claims 18 or 19 wherein the heating in step (c) is carried out at a temperature of about 80° C.

24. A process according to claim 23 wherein the heating in step (c) is carried out for a period of from one to 72 hours.

25. A process according to claim 20 wherein the heating in step (c) is carried out for at least four hours.

26. A process according to claim 23 wherein said monitoring is carried out by infrared analysis.

27. A process according to claim 26 wherein cooling is carried out to a temperature of 40° C. or less after obtaining a conversion of from 10 to 90% to the beta form whereby a product containing from 10 to 90% beta and 90 to 10% alpha is obtained.

* * * * *